United States Patent [19]
Shemesh et al.

[11] Patent Number: 5,836,619
[45] Date of Patent: Nov. 17, 1998

[54] MANUALLY-SEVERABLE COUPLING DEVICE, AND MEDICAL INFUSION ASSEMBLY INCLUDING SAME

[75] Inventors: Eli Shemesh, Ashdod; Ellen Tobe, Tel Aviv, both of Israel

[73] Assignee: Migada, Inc., Englewood Cliffs, N.J.

[21] Appl. No.: 637,771

[22] PCT Filed: Oct. 28, 1994

[86] PCT No.: PCT/US94/12439

§ 371 Date: Jul. 22, 1996

§ 102(e) Date: Jul. 22, 1996

[87] PCT Pub. No.: WO95/12780

PCT Pub. Date: May 11, 1995

[30] Foreign Application Priority Data

Nov. 5, 1993 [IL] Israel ....................................... 107509

[51] Int. Cl.⁶ .............................. F16L 37/28; A61M 1/28
[52] U.S. Cl. ............................ 285/4; 285/131.1; 604/29; 604/905; 604/244
[58] Field of Search ................................ 285/3, 4, 125.1, 285/131.1; 604/905, 200, 244, 283, 29; 137/797; 403/2

[56] References Cited

U.S. PATENT DOCUMENTS

| | | | |
|---|---|---|---|
| 3,127,892 | 4/1964 | Bellamy, Jr. et al. | |
| 3,217,710 | 11/1965 | Beall et al. | |
| 3,342,179 | 9/1967 | Ellmann | 128/214.2 |
| 4,776,849 | 10/1988 | Shinno et al. | 604/283 |
| 4,899,903 | 2/1990 | Miyasaka et al. | 220/266 |
| 5,045,067 | 9/1991 | Ohnaka et al. | 604/244 |
| 5,221,267 | 6/1993 | Folden | 604/200 |
| 5,259,843 | 11/1993 | Watanabe et al. | 604/256 |
| 5,336,173 | 8/1994 | Folden | 604/29 |

FOREIGN PATENT DOCUMENTS 511483  6/1967  Belgium .

OTHER PUBLICATIONS

Military Standarlization Handbook—Plastics MIL-H-DBK—700 [MR] pp. 35–41, Nov. 1965.

*Primary Examiner*—Heather Shackelford
*Attorney, Agent, or Firm*—Ladas & Parry

[57] ABSTRACT

A manually-severable coupling device for coupling two tubes (12a, 12b), particularly useful in peritoneal dialysis, including a flexible plastic member having passageways (30) therethrough and formed with tubular end sections (31, 32) for receiving tubes (20, 24) to be coupled, an annular groove (33) formed intermediate the tubular end sections defining a flexible, weakened, annular web (33) capable of being severed by rotating one of the tubular end sections (31, 32) with respect to the other, and a finger gripping formation (34, 35) integrally formed in each tubular end section (31, 32) on opposite sides of the weakened annular web (33) grippable by a user to rotate the tubular end sections with respect to each other to sever them from each other along the weakened annular web (33).

8 Claims, 2 Drawing Sheets

MANUALLY-SEVERABLE COUPLING DEVICE, AND MEDICAL INFUSION ASSEMBLY INCLUDING SAME

The present invention relates to a manually-severable coupling device for coupling two tubes. The invention is particularly applicable in medical infusion assemblies such as are used in peritoneal dialysis (PD), and is therefore described below with respect to such an application.

Many of the treatments used today in medical practice involve infusing solutions into the patient and/or draining fluids from the patient. Such treatments includes inserting an invasive device such as a catheter or needle into the patient, carrying out the treatment, and removing the invasive device. In the event that numerous such treatments are necessary, a catheter is used implanted, and the vessel or bag used for the treatment is connected to and disconnected from the implanted catheter. However, the numerous manipulations involved greatly increase the danger of infective agents entering the body at the site of the catheter. Any reduction, therefore, in the number of manipulations at the catheter inlet can be expected to lead to a corresponding lessening of the risk of infection.

One of the treatments commonly used for patients suffering from prolonged renal failure is Continuous Ambulatory Peritoneal Dialysis (CAPD). In CAPD, a sterile dialysis solution is infused into the peritoneal cavity of the patient via an implanted catheter. Following an equilibration period of a few hours, during which waste products of the body diffuse into the solution, the waste-containing solution is drained from the cavity and a fresh solution is introduced.

The above procedure is normally performed by the patient on an ambulatory basis, and involves a number of connections and disconnections which must be performed under strictly aseptic conditions. One of the major problems plaguing peritoneal dialysis (PD) is the infection of the peritoneal cavity (peritonitis) caused by breaches in the aseptic connection procedure. These infections may become severe, and at times may result in removal of the patient from the dialysis program.

Many improvements in CAPD have been introduced over the years to reduce the risk of contracting peritonitis. One of these was the development of the "double bag" system, in which a closed sterile system includes both an empty drainage bag and a full solution bag. This system obviates the use of separate connection tubing for each of the bags, thus reducing the number of connections and disconnections. When using this system, the inlet port of the implanted catheter is exposed to the environment only twice during one treatment cycle: once when a new PD set is connected to the catheter, and once when the set is disconnected.

A further development in this field was recently described in U.S. Pat. No. 5,221,267 to Folden. In that system, a friable tube coupling, manually breakable in a snap manner by a bending force, is positioned adjacent to the end of the PD set which is connected to the catheter. Following infusion of the sterile solution, the patient permanently clamps the tubing section interposed between the catheter and the coupling, and then disconnects the infusion system by bending the coupling until it breaks. This reduces the number of exposures of the catheter by 50%. Before the next fluid exchange, the patient simply disconnects the tubing stump from the previous exchange and connects a new set.

Although the system of Folden decreases the risk of infection, it contains a number of disadvantages. The friable tubing must not be too difficult to break so as to be suitable for patients in a weakened condition. On the other hand, if the tubing can be broken too easily, it may break accidentally before the end of dialysis. This is of course very dangerous, as in such a case sterility is suspended and infection may result. In addition, jagged ends of the coupling can wound the patient, introducing infection in that manner. Finally, the rigidity of the coupling makes it unwieldy in view of the various manipulations necessary during the dialysis treatment.

An object of the present invention is to provide a manually-severable coupling device having advantages in the above respects. Another object of the invention is to provide a medical infusion assembly including such a coupling device.

In accordance with the present invention, there is provided a manually-severable coupling device for coupling two tubes, comprising a flexible plastic member having a passageway therethrough and formed with plastic end sections at its opposite ends for receiving the tubes to be coupled; an annular groove formed in the flexible plastic member intermediate its tubular end sections defining a flexible, weakened, annular web capable of being severed by rotating the tubular end sections with respect to the other; and a finger gripping formation integrally formed in each of the tubular end sections on opposite sides of the weakened annular web, grippable by a user to rotate the tubular end sections with respect to each other to sever them from each other along the weakened annular web.

As will be described more particularly below, such a coupling device avoids the many disadvantages described above, particularly when used in a medical infusion assembly for peritoneal dialysis. Thus, the device may be attached to the catheter end of the dialysis tubing, usually by gluing, so that it becomes an integral complement of the dialysis infusion assembly. The flexibility of the coupling device allows for bending and twisting to a substantial degree without damage, thereby imposing a minimum of interference and inconvenience during the dialysis treatment. In order to sever the coupling device, the finger gripping formations formed on the opposite sides of the weakened annular web are manually gripped and rotated with respect to each other, e.g. for more than 90 degrees, to sever the annular web. This severing operation is simple and requires very little force. Furthermore, no jagged ends result from the severing.

According to another aspect of the invention, there is provided a medical infusion assembly, comprising: a first tube for connection to an infusion liquid bag for supplying an infusion liquid to a subject; a second tube for connection to the subject to receive the infusion liquid; and a manually-severable coupling device as described above connecting the first tube to the second tube.

Further features and advantages of the invention will be apparent from the description below.

The invention is herein described, by way of example only, with reference to the accompanying drawings, wherein.

Figure 5:
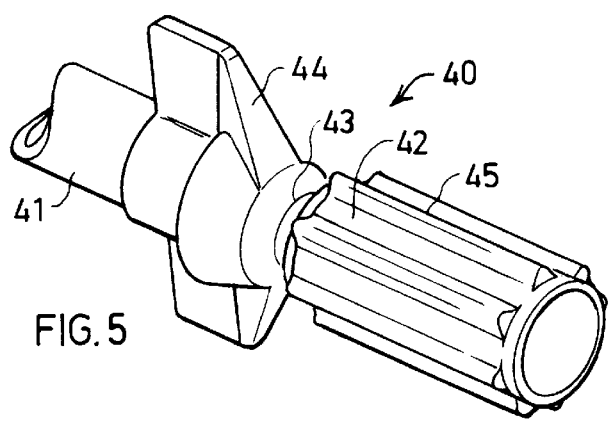

and FIG. 5 is a perspective view of a another form of manually-severable coupling device constructed in accordance with the present invention.

Figure 1:
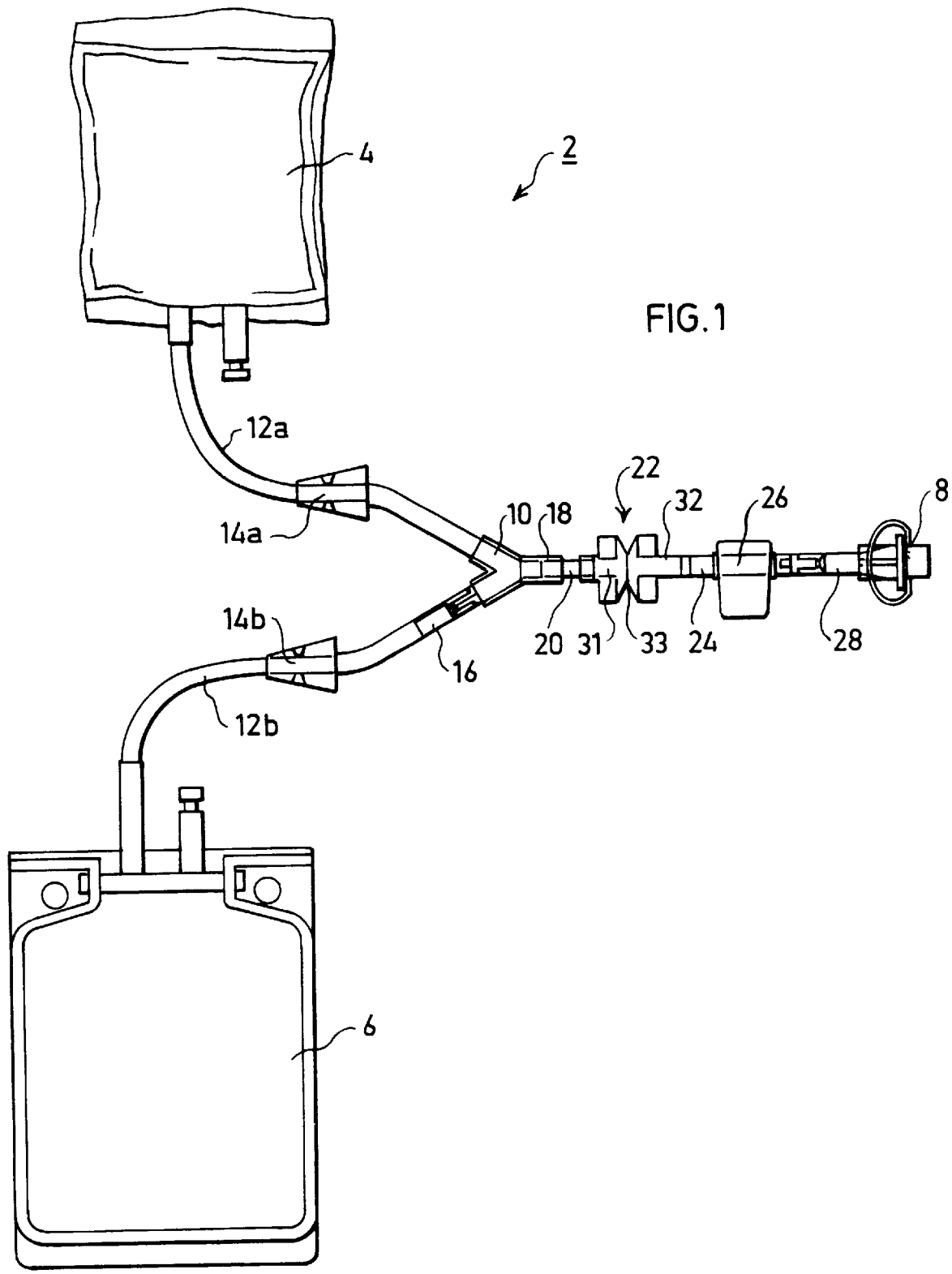
FIG. 1 illustrates a double-bag peritoneal dialysis (PD) infusion assembly constructed in accordance with the present invention.

Referring to FIG. 1, there is illustrated a double-bag peritoneal dialysis (PD) system, generally designated 2, including a medical infusion assembly, and particularly a manually-severable coupling device, constructed in accordance with the present invention. The illustrated system 2 includes an infusion liquid bag 4 containing fresh dialysate solution to be introduced into the patient, an empty drainage bag 6 for receiving the waste-containing dialysate from the peritoneal cavity, and a catheter attachment port 8 for attaching the system to the catheter set (not shown). Each of the bags 4,6 of the system is connected to one port of a Y-coupling 10 by branch tubes 12a and 12b each including a reversible clamp 14a,14b for opening one of the tubes, while the other is closed. A break-away cannula 16 is further included in branch tube 12b to the drainage bag 6. Break-away cannula 16 is effective normally to close the passage via branch tube 12b to the drainage bag 6, but may be manually broken away to open this passage. Such break-away cannulas are well known, and therefore further details of its construction are not set forth herein.

The Y-connector 10, via its common port 18, connects the two branch tubes 12a,12b to a common tube 20 such that the two branch tubes 12a,12b may be selectively opened or closed by their respective clamps 14a,14b. Tube 20 is in turn connected, via a manually-severable coupling device generally designated 22, to another tube 24, which is in turn connected to the catheter attachment port 8. The latter tube 24 further includes a single-closure clamp, i.e. a clamp (of known construction) which is normally open, manually closable, and non-openable thereafter once it has been manually closed. Tube 24 leading to the catheter attachment port 8 also includes another break-away cannula 28.

Figure 2:
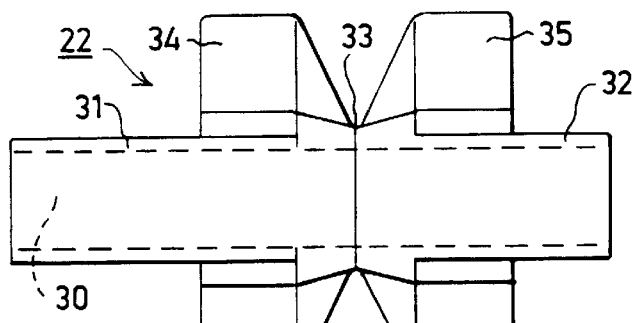
FIG. 2 is an enlarged side elevational view illustrating the manually-severable coupling device included in the assembly of FIG. 1.
Figure 3:
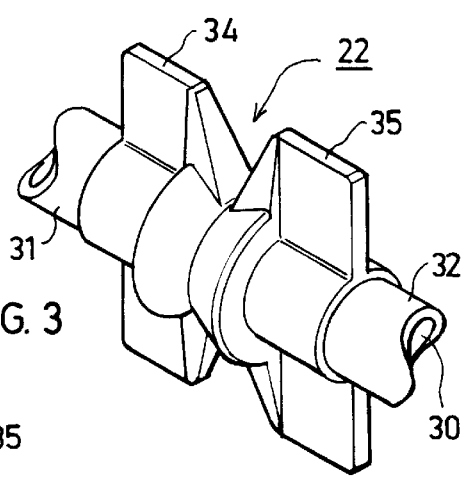
FIG. 3 is a perspective view of the coupling device of FIG. 2.

The manually-severable coupling device, generally designated 22 in FIG. 1, is more particularly illustrated in FIGS. 2 and 3. It is a one-piece, flexible plastic member having a through-going passageway 30 and integrally formed with tubular end sections 31,32 at its opposite ends for receiving the two tubes 20,24 of the infusion assembly illustrated in FIG. 1. Examples of materials that could be used for member 22 are soft polyethylene and soft polypropylene. Member 22 is further formed with an annular groove 33 intermediate the two tubular end sections 31,32. Groove 33 defines a flexible, weakened, annular web capable of being severed by rotating one of the end sections 31,32 with respect to the other. A finger gripping formation 34,35 is further integrally formed in each of the end sections 31,32 on opposite sides of the weakened annular web 33, grippable by a user to rotate the end sections with respect to each other in order to sever the two end sections along the web 33.

Figure 4:
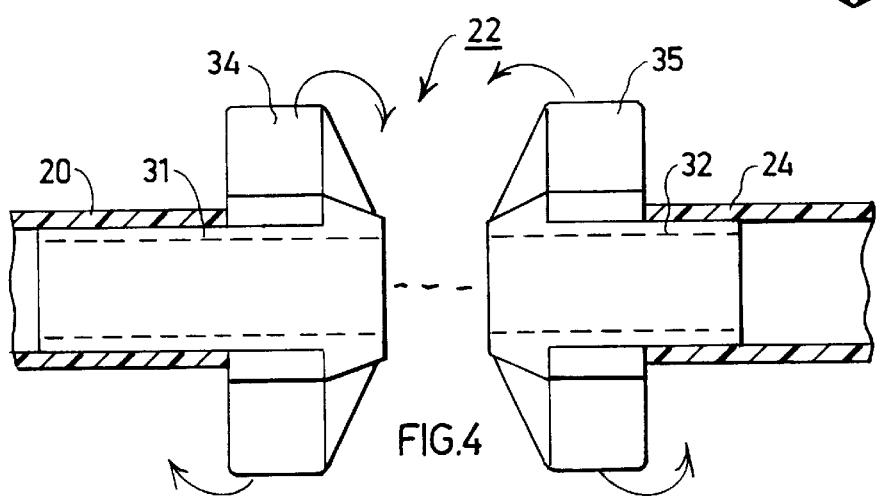
FIG. 4 is a side elevational view illustrating the coupling device of FIGS. 2 and 3 after it has been manually severed.

In the embodiment illustrated in FIGS. 2 and 3, each finger gripping formation 34,35, formed in the end sections 31,32, includes a pair of radially projecting ears or wings, one engageable by the thumb and the other by the index finger of the person severing the coupling device. When the coupling device is to be severed, as will be described more particularly below, the person grips the pair of wings of one section with one hand, and the pair of wings of the other section with the other hand, and then rotates one section with respect to the other until the coupling device 22 is severed along the weakened web 33. FIG. 4 illustrates the coupling device when so severed.

Following is a description of one manner of using the system illustrated in FIG. 1 for peritoneal dialysis (PD) of a patient having a catheter set implanted in the patient's peritoneal cavity. It will be assumed that the peritoneal cavity had been previously filled with a dialysate solution where it has remained for a sufficient time to receive by diffusion the waste products of the body, and now it is ready to drain the waste-containing solution from the peritoneal cavity and to introduce a fresh solution.

The PD set illustrated in FIG. 1, including a fresh solution bag 4, an empty drainage bag 6, and the tubing assembly containing the manually-severable coupling device 22, is connected to the patient's catheter set via the catheter attachment port 8. The single-closure clamp 26 is open, and the two clamps 14a,14b in the branches 12a,12b to the solution bag 4 and drainage bag 6, respectively, are closed.

The two break-away cannulas 28 and 16 are then broken away; the drainage bag 6 is lowered below the patient's peritoneal cavity; and clamp 14b in branch 12b is opened. This permits the dialysate containing the waste materials to be gravity-fed from the peritoneal cavity into the drainage bag 6 via attachment port 8, open clamp 26, coupling device 22 and branch 12b of Y-connector 10.

On completion of the drainage, clamp 14b is closed; the solution bag 4 is raised above the peritoneal cavity, and clamp 14a in branch 12a to the solution bag 4 is opened. This allows the fresh dialysate solution to flow by gravity from bag 4 into the peritoneal cavity via branch 12a, Y-coupling 10, coupling device 22, open clamp 26 and attachment port 8.

When the solution bag has emptied, the single-closure clamp 26 is now closed. As indicated earlier, once this clamp is closed, it can no longer be reopened. Accordingly, the peritoneal cavity is now permanently disconnected from either solution bag 4 or the drainage bag 6. These two bags, together with the portion of the tubing assembly connecting them to coupling device 22, may therefore be removed by manually severing the coupling device 22. This is done by placing the index finger and thumb of one hand on the opposite sides of the two wings 34 on one side of the weakened web 33, and placing the index finger and thumb of the other hand on opposite sides of the wings 35 on the other side of web 33, and then rotating the two wings with respect to each other until the coupling device 22 severs along the web 33. The web is preferably of a thickness and of a material such that it will tear upon rotating the two tube sections 31,32, integrally formed with the two wings 34,35, an angular amount of more than 90°, (e.g., from 90°–360°). Because of the pliability of this material, this severing action can be performed with very little exertion and requires no special implements such as a scissors or knife. The torn edges of the so-severed tube sections 31,32 are not dangerous because of the softness and flexibility of the plastic material of which the coupling device 22 is made.

Since tube 24 adjacent to the catheter set is clamped closed by the single-closure clamp 26, disconnecting the used PD set from the patient in the above-described manner does not involve exposure of the peritoneal cavity to possible infection. The residual portion of the PD set remaining attached to the patient is relatively short and is also flexible so that it does not interfere with the patient's activities during the dwell time of the dialysate in the peritoneal cavity.

At the end of the dwell period, the catheter attachment port 8 is detached from the catheter set (for example by unscrewing), and a new PD set can then be attached. This is the only time during the dialysis cycle when the cavity is exposed to the environment.

FIG. 5 illustrates a variation in the construction of the coupling device 22. In this variation, the finger-gripping formation integrally formed in tubular extension 41 on one side of the annular web 43 also includes a pair of radially projecting wings, as shown at 44 in FIG. 5. However, the finger-gripping formation of the other tubular end section 42 is in the form of a plurality of axially-extending circumferentially-spaced ribs 45 having an outer effective diameter substantially smaller than that of the pair of radially-projecting wings 44. The tubular end section 42 formed with the smaller-diameter ribs 45 would receive tube 24 which remains attached to the patient when the remainder of the system has been severed as described above, and therefore would even further decrease the possible interference or inconvenience to the subject by retaining this residual part of the set attached to the patient during the dialysate dwell period.

Many other variations, modifications and applications of the invention will be apparent.

We claim:

1. A medical infusion assembly particularly useful for peritoneal dialysis, comprising:
    a first tube for connection to an infusion liquid bag for supplying an infusion liquid to a subject;
    a second tube for connection to the subject to receive the infusion liquid; and
    a manually-severable coupling device which couples said first and second tubes, comprising:
        a flexible plastic member having a passageway therethrough and formed with tubular end sections at its opposite ends for receiving the tubes to be coupled;
        an annular groove formed in said flexible plastic member intermediate its tubular end sections defining a flexible, weakened annular web, said weakened annular web capable of being severed by rotating one of said tubular end sections with respect to the other; and a finger gripping formation integrally formed in each of said tubular end sections on opposite sides of said weakened annular web, grippable by a user to rotate said tubular end sections with respect to each other to sever them from each other along said weakened annular web,
    wherein said first tube includes one branch connectable to said infusion liquid bag, a second branch connectable to a liquid drainage bag for draining a liquid, and a clamp in each of said branches which selectively opens either of said first or second branches while the other is closed, wherein said first tube is connected to said first and second branches by a Y-connector and wherein at least one of the branches of the first tube includes a breakaway cannula.

2. The coupling device according to claim 1, wherein said finger gripping formation integrally formed in at least one of said tubular end sections includes a pair of radially projecting wings engageable by the thumb and index finger, respectively, of a person severing the coupling device by rotating said end sections.

3. The coupling device according to claim 1, wherein said finger gripping formation integrally formed in both of said tubular end sections includes a pair of radially projecting wings engageable by the thumb and index finger, respectively, of a person severing the coupling device by rotating said end sections.

4. The coupling device according to claim 1, wherein said finger gripping formation integrally formed in at least one of said tubular end sections includes a plurality of axially-extending circumferentially-spaced ribs engageable by the thumb and index finger, respectively, of a person severing the coupling device by rotating said end sections.

5. The coupling device according to claim 1, wherein said finger gripping formation integrally formed in one of said tubular end sections includes a pair of radially-projecting wings engageable by the thumb and index finger, respectively, of one hand of a person severing the coupling device; and the finger gripping formation integrally formed in the other of said tubular end sections includes a plurality of axially-extending circumferentially-spaced ribs engageable by the thumb and index finger, respectively, of the other hand of the person severing the coupling device; said plurality of radially-extending circumferentially-spaced ribs having an outer effective diameter substantially smaller than that of said pair of radially-projecting wings.

6. The medical infusion assembly according to claim 1, wherein said second tube includes a valve which is normally opened, manually closable, and non-openable once it has been manually closed.

7. The medical infusion assembly according to claim 1, wherein, in the manually-severable coupling device, said finger gripping formation connected to said first tube includes a pair of radially-projecting wings engageable by the thumb and index finger, respectively, of one hand of a person severing the coupling device; and the finger-gripping formation integrally formed in the tubular end section connected to said second tube includes a plurality of axially-extending circumferentially-spaced ribs engageable by the thumb and index finger, respectively, of the other hand of the person severing the coupling device; said axially-extending circumferentially-spaced ribs having an outer effective diameter substantially smaller than that of said pair of radially-projecting wings.

8. A peritoneal dialysis system comprising:
    (i) an infusion liquid bag containing fresh dialysate solution, said liquid infusion bag being communicatively connected one port of a Y-coupling;
    (ii) a drainage bag for receiving waste-containing dialysate from the peritoneal cavity, said drainage bag being communicatively connected to a second port of said Y-coupling; and
    (iii) a manually-severable coupling device for coupling two tubes according to claim 1.

* * * * *